(12) United States Patent
Grammenos et al.

(10) Patent No.: US 6,693,124 B1
(45) Date of Patent: Feb. 17, 2004

(54) BISIMINO-SUBSTITUTED PHENYL COMPOUNDS AND THEIR USE AS PESTICIDES

(75) Inventors: Wassilios Grammenos, Ludwigshafen (DE); Herbert Bayer, Mannheim (DE); Thomas Grote, Schifferstadt (DE); Hubert Sauter, Mannheim (DE); Andreas Gypser, Mannheim (DE); Reinhard Kirstgen, Neustadt (DE); Bernd Müller, Frankenthal (DE); Arne Ptock, Ludwigshafen (DE); Franz Röhl, Schifferstadt (DE); Gisela Lorenz, Neustadt (DE); Eberhard Ammermann, Heppenheim (DE); Siegfried Strathmann, Limburgerhof (DE); Volker Harries, Frankenthal (DE)

(73) Assignee: BASF Aktiengesellschaft, Ludwigshaften (DE)

( * ) Notice: Subject to any disclaimer, the term of this patent is extended or adjusted under 35 U.S.C. 154(b) by 0 days.

(21) Appl. No.: 09/445,313

(22) PCT Filed: May 29, 1998

(86) PCT No.: PCT/EP98/03229

§ 371 (c)(1),
(2), (4) Date: Dec. 6, 1999

(87) PCT Pub. No.: WO98/56774

PCT Pub. Date: Dec. 17, 1998

(30) Foreign Application Priority Data

Jun. 9, 1997 (DE) .......................... 197 24 200

(51) Int. Cl.[7] ..................... A01N 43/80; A01N 43/653; C07D 249/12; C07D 261/12
(52) U.S. Cl. ....................... 514/380; 514/384; 548/243; 548/263.6; 548/263.8; 548/264.4; 548/264.6
(58) Field of Search ................. 514/384, 380; 548/263.6, 263.8, 264.4, 264.6, 243

(56) References Cited

U.S. PATENT DOCUMENTS 5,780,050 A     7/1998  Jain et al.
6,207,692 B1 *  3/2001  Muller et al. ............... 514/384

FOREIGN PATENT DOCUMENTS

| CA | 2232374 | 5/1986 |
| CA | 2224887 | 2/1997 |
| WO | 95/21153 | 8/1995 |
| WO | 97/02255 | 1/1997 |
| WO | 97/05103 | 2/1997 |
| WO | 97/15552 | 5/1997 |

* cited by examiner

Primary Examiner—Patricia L. Morris
(74) Attorney, Agent, or Firm—Keil & Weinkauf

(57) ABSTRACT

Bisimino-substituted phenyl compounds of the formula I

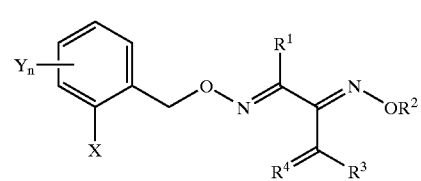

where the substituents have the following meanings:
X is a group A or B

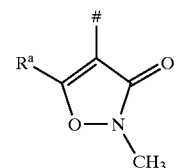

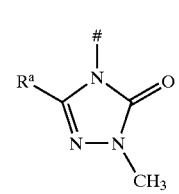

where
\# denotes the bond with the phenyl ring and
$R^a$ is halogen, alkyl or alkoxy;
Y is halogen, alkyl, haloalkyl or alkoxy;
n is 0, 1 or 2, it being possible for the radicals Y to be different if n=2;
$R^1$ is alkyl;
$R^2$ is alkyl, haloalkyl, alkenyl, haloalkenyl, alkynyl or haloalkynyl;
$R^3$ is hydrogen, alkyl, haloalkyl or substituted or unsubstituted phenyl;
$R^4$ is $=CR^bR^c$ or $=N-OR^d$ where
 $R^b$, $R^c$ independently of one another are hydrogen, alkyl or substituted or unsubstituted phenyl; and
 $R^d$ is one of the radicals mentioned under $R^2$.

Processes and intermediates for their preparation, and their use.

20 Claims, No Drawings

BISIMINO-SUBSTITUTED PHENYL COMPOUNDS AND THEIR USE AS PESTICIDES

The present invention relates to a bisimino-substituted phenyl compound of the formula I

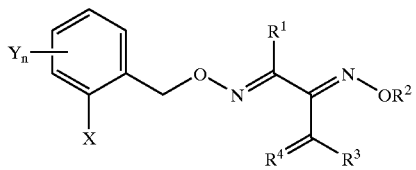

where the substituents have the following meanings:
X is a group A or B

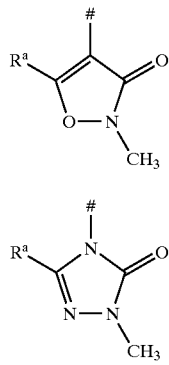

where
# denotes the bond with the phenyl ring and
$R^a$ is halogen, $C_1$–$C_4$-alkyl or $C_1$–$C_4$-alkoxy;
Y is halogen, $C_1$–$C_4$-alkyl, $C_1$–$C_4$-haloalkyl or $C_1$–$C_4$-alkoxy;
n is 0, 1 or 2, it being possible for the radicals Y to be different if n=2;
$R^1$ is $C_1$–$C_4$-alkyl;
$R^2$ is $C_1$–$C_4$-alkyl, $C_1$–$C_4$-haloalkyl, $C_3$–$C_4$-alkenyl, $C_3$–$C_4$-haloalkenyl, $C_3$–$C_4$-alkynyl or $C_3$–$C_4$-haloalkynyl;
$R^3$ is hydrogen, $C_1$–$C_4$-alkyl, $C_1$–$C_4$-haloalkyl or substituted or unsubstituted phenyl;
$R^4$ is $=CR^bR^c$ or $=N-OR^d$ where
$R^b$, $R^c$ independently of one another are hydrogen, $C_1$–$C_6$-alkyl or substituted or unsubstituted phenyl; and
$R^d$ is one of the radicals mentioned under $R^2$.

In addition, the invention relates to processes and intermediates for the preparation of the compounds I, and to compositions and to the use of the compounds I for controlling harmful fungi and animal pests.

WO-A 97/02,255 discloses 4-phenyl-2,3-dihydroisoxazolones and 4-phenyl-2,4-dihydrotriazolones with a methoxyimino group in the ortho-position.

WO-A 95/21,153 and WO-A 97/05,103 describe α-phenylacrylic acid and α-phenyl-α-methoxyiminoacetic acid derivatives with a bisoxime ether group in the ortho-position, and PCT/EP 96/04,446 describes such derivatives which have a trisoxime ether group.

The compounds described in the documents mentioned above are suitable as crop protection agents against harmful fungi and, in some cases, against animal pests.

However, their action is not satisfactory in many cases. It is an object of the invention to provide compounds with an improved activity.

We have found that this object is achieved by the phenyl compounds of the formula I. We have furthermore found intermediates and processes for the preparation of the compounds I, and the use of the compounds I and of compositions comprising them for controlling harmful fungi and animal pests. The fungicidal action is preferred.

The compounds of the formula I differ from the compounds disclosed in the above document WO-A 97/02,255 in as far as the oximino group is substituted by a radical $R^4$ which is bonded to a double bond and which cannot be hydrogen. Compared with the known compounds, the compounds of the formula I have a better activity against harmful fungi and animal pests.

In principle, the compounds of the formula I can be obtained using similar methods to those described in WO-A 97/02,255, WO-A 95/21,153 and WO-A 97/05,103 and in PCT/EP 96/04,446.

The compounds I can be obtained by various routes, it being immaterial for the synthesis whether it is the group X or the oxime ether group which is synthesized first. In the descriptions of the reactions which follow, therefore, the term $X^\#$ will be used for the radical X or a suitable precursor of this radical and $E^\#$ for the oxime ether group or a suitable precursor, for reasons of better readability.

In particular, compounds of the formula I.1

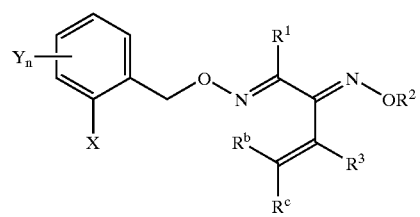

are obtained by converting a benzyl compound of the formula $II^\#$ with an oxime of the formula III and converting the resulting oxime ether of the formula $IV^\#$ into the halogen compound of the formula $V^\#$ by means of halogenation, reacting $V^\#$ with a hydroxylamine ether of the formula VI' to give the bisoxime of the formula $VI^\#$, oxidizing $VI^\#$ to give the carbonyl compound of the formula $VII^\#$, and reacting $VII^\#$ with a phosphorus reagent following the principles of Wittig reaction to give a compound of the formula $I.1^\#$.

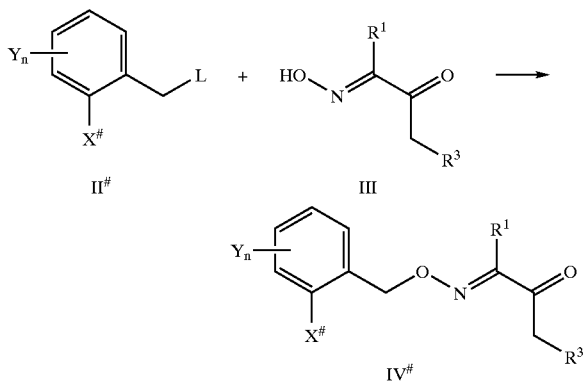

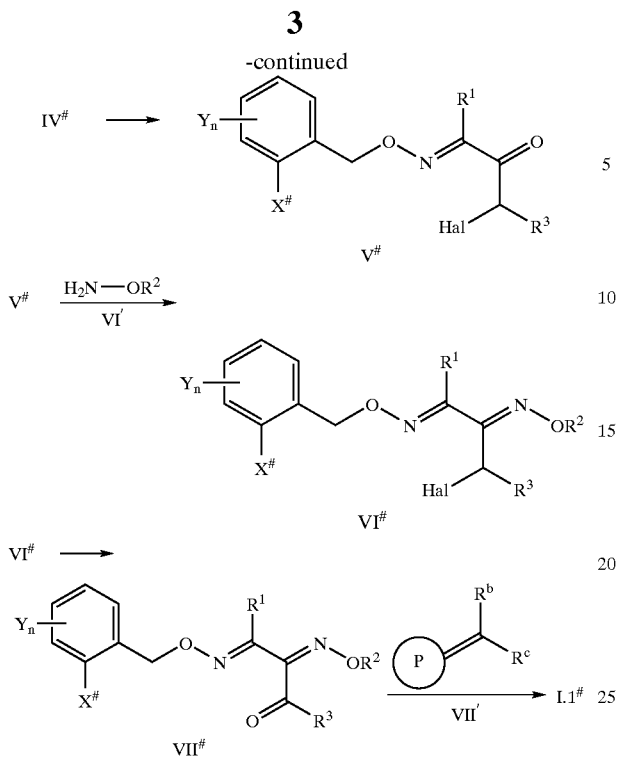

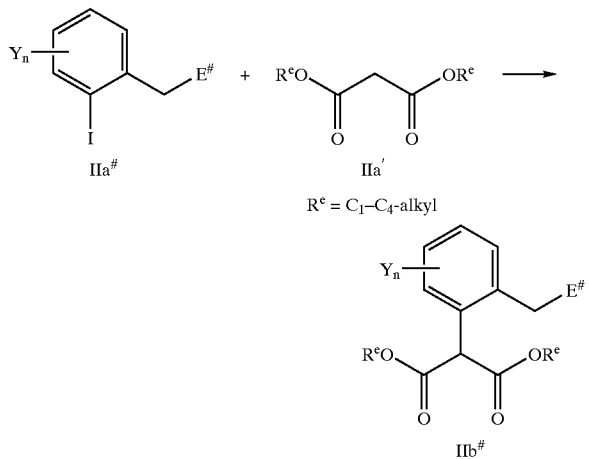

$R^e = C_1-C_4\text{-alkyl}$

In formula II#, L is a nucleophilically exchangeable group, for example halogen, such as fluorine, chlorine, bromine or iodine, in particular chlorine or bromine, or alkyl- or arylsulfonates, such as mesylate or tosylate.

In the above equation, (P) in formula VII' is a phosphoranyl dical such as, for example, triphenylphosphoranyl.

1. The reaction of the benzyl compound II# with the oxime of the formula III# is carried out in a manner known per se at from −10° C. to 100° C., preferably 10° C. to 85° C., in an inert organic solvent in the presence of a base [cf. WO-A 97/02,255; WO-A 96/36,229].

Suitable solvents are ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethylformamide and dimethylacetamide, particularly preferably tetrahydro-furan, acetonitrile and dimethylformamide. Mixtures of the solvents mentioned may also be used.

Suitable bases are, generally, inorganic compounds such as alkali metal hydroxides and alkaline earth metal hydroxides such as lithium hydroxide, sodium hydroxide, potassium hydroxide and calcium hydroxide, alkali metal hydrides and alkaline earth metal hydrides such as lithium hydride, sodium hydride, potassium hydride and calcium hydride, alkali metal carbonates and alkaline earth metal carbonates such as lithium carbonate, potassium carbonate and calcium carbonate, and also alkali metal hydrogen carbonates such as sodium hydrogen carbonate, alkali metal alkoxides and alkaline earth metal alkoxides such as sodium methoxide, sodium ethoxide, potassium ethoxide, potassium tert-butoxide and dimethoxy-magnesium, furthermore organic bases, eg., tertiary amines such as trimethylamine, triethylamine, triisopropylethyl-amine and N-methylpiperidine, pyridine, substituted pyridines such as collidine, lutidine and 4-dimethylaminopyridine, and also bicyclic amines. Particularly preferred are sodium hydride, potassium carbonate and sodium methoxide.

The bases are generally employed in catalytic amounts, but they may also be used in equimolar amounts, in an excess or, if appropriate, as the solvent.

The starting materials are generally reacted with each other in equimolar amounts. It may be advantageous for the yield to employ III in an excess based on II#.

The benzyl compounds II# which are required for the preparation of the compounds I are disclosed in the literature [cf. WO-A 97/02,255]. They can be obtained by the following synthesis route:

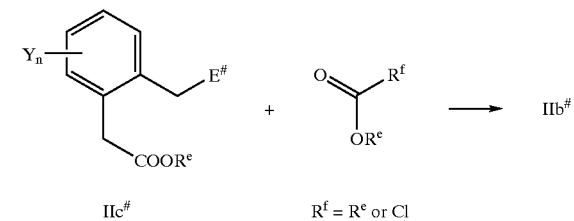

$R^f = R^e \text{ or Cl}$

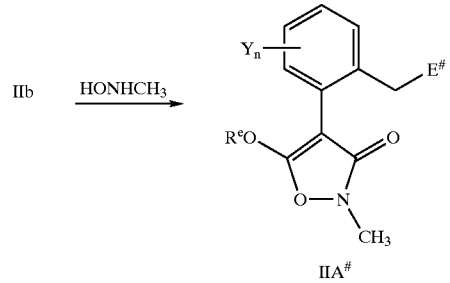

Compounds of the formula IIA# where $R^a$ is alkyl are obtained in the manner disclosed in U.S. Pat. No. 4,952,573 from corresponding phenylacetic acid esters IIc#.

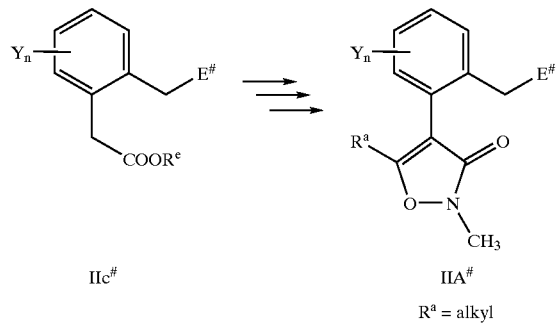

$R^a = \text{alkyl}$

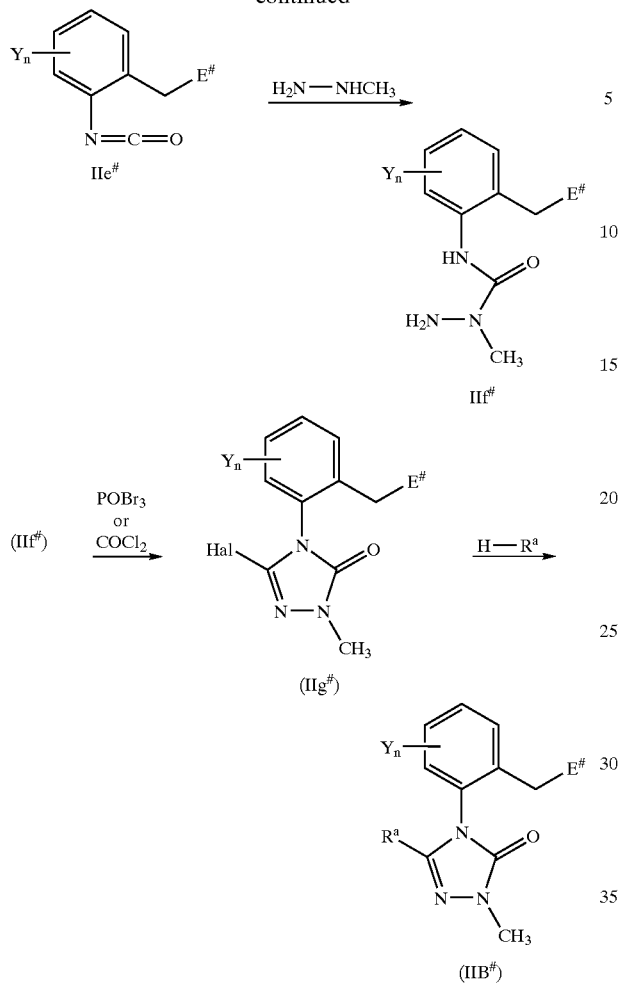

This route is not only suitable for the preparation of the benzyl compounds II#, but, in principle, suitable for synthesizing the groups A or B at each synthesis level of the oxime ether group E#. The group X is particularly preferably synthesized at the level of the compounds IIa or IIe where E# is hydrogen.

The benzyl compounds IIB# required for the preparation of the compounds IB where $R^a$ is alkyl which are not known from the literature [cf. WO-A 96/36229] can be obtained using methods similar to those of the literature [cf. J. Org. Chem., Vol. 43 (1978), p. 936]. They can be obtained by reacting the carbamates of the formula IIf# with orthoesters:

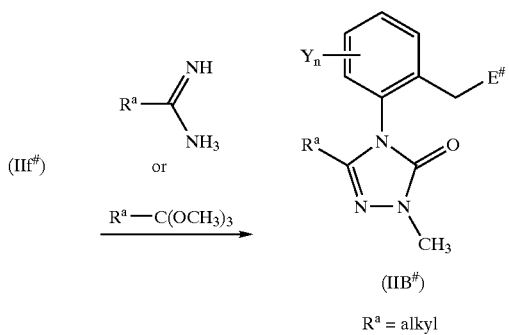

Those oximes of the formula III which are not already known from the literture [cf. EP-A 95/21,153] can be prepared in accordance with the literature cited.

2. Halogenation of the oxime ether IV# is usually carried out at from −10° C. to 80° C., preferably 0° C. to 65° C., in an inert organic solvent in the presence or absence of an acid. J. Org. Chem. (1981), p. 2532; Org, Synth., Vol. 55 (1976), p. 24; Tetrahedron (1970) p. 5611].

Suitable halogenating agents are bromine, chlorine, pyridin*$HBr_3$, $CuBr_2$ and $SO_2Cl_2$, in particular bromine, $CuBr_2$ and $SO_2Cl_2$. They are generally reacted with each other in equimolar amounts. It may be advantageous for the yield to employ them in a 1.2- to 2.5-fold excess based on the compound IV#.

Suitable solvents are aromatic hydrocarbons such as toluene, o-, m- and p-xylene, halogenated hydrocarbons such as methylene chloride, chloroform and chlorobenzene, and also alcohols such as methanol, ethanol, n-propanol, isopropanol, n-butanol and tert-butanol, particularly preferably cyclohexane, methylene chloride, chloroform, chlorobenzene and methanol. Mixtures of these may also be used.

Acids and acidic catalysts which are used are inorganic acids such as hydrochloric acid, hydrobromic acid and sulfuric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid.

The acids are generally employed in catalytic amounts, but they can also be used in equimolar amounts, in an excess or, if appropriate, as the solvent.

The starting materials are generally reacted with each other in equimolar amounts. It may be advantageous for the yield to employ the halogenating agent in an excess based on IV#.

3. The reaction of the oxime ether V# with the hydroxylamine ether of the formula VI' to give the bisoxime ether VI# is carried out in a known manner at from 0° C. to 85° C., preferably at from 20° C. to 65° C., in an inert organic solvent.

4. The oxidation of the bisoxime ether VI# is carried out in a known manner at from 20° C. to 160° C., preferably at from 20° C. to 100° C., in an inert organic solvent, in the presence or absence of a base [cf. Houben-Weyl, Methoden der organischen Chemie [Methods in organic chemistry], Volume E3, pp. 247–265, Georg Thieme Verlag, Stuttgart 1983].

Examples of suitable oxidants are N-methylmorpholine N-oxide, 2-benzoyl-1-trifluoromethanesulfonylhydrazine, trimethylamine N-oxide and pyridine N-oxide, in particular N-methylmorpholine N-oxide, trimethylamine N-oxide and pyridine N-oxide.

Suitable bases are, generally, inorganic compounds such as alkali metal hydroxides and alkaline earth metal hydroxides such as lithium hydroxide, sodium hydroxide, potassium hydroxide and calcium hydroxide, alkali metal carbonates and alkaline earth metal carbonates such as lithium carbonate, potassium carbonate and calcium carbonate, and also alkali metal hydrogen carbonates such as sodium hydrogen carbonate, moreover organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Particularly preferred are sodium hydroxide, sodium hydrogen carbonate and potassium carbonate.

The bases are generally employed in catalytic amounts, but they can also be used in equimolar amounts, in an excess or, if appropriate, as the solvent.

The starting materials are generally reacted with each other in equimolar amounts. It may be advantageous for the yield to employ the oxidant in an excess based on VI#.

5. The Wittig reaction is carried out in a known manner at from −78° C. to 85° C., preferably −10° C. to 65° C., in an inert organic solvent in the presence of a base [cf. EP-A 513 580].

The reaction mixtures are worked up in the customary manner, eg. by mixing with water, separating the phases and, if appropriate, purifying the crude products by chromatography. Some of the intermediates and end products are obtained in the form of colorless or pale brown viscous oils which are purified or freed from volatile components under reduced pressure and at a moderately elevated temperature. If the intermediates and end products are obtained as solids, they may also be purified by recrystallization or digestion. Those starting materials of the formula III required for the preparation of the compounds I which are not already known from the literature [J. Org. Chem. (1991), p. 2605; Bull. Soc. Chim. Fr. (1973), p. 1452] can be prepared in accordance with the literature cited.

Compounds of the formula I.2 are obtained for example by reacting a carbonyl compound of the formula VI# with a hydroxylamine ether of the formula VIII#.

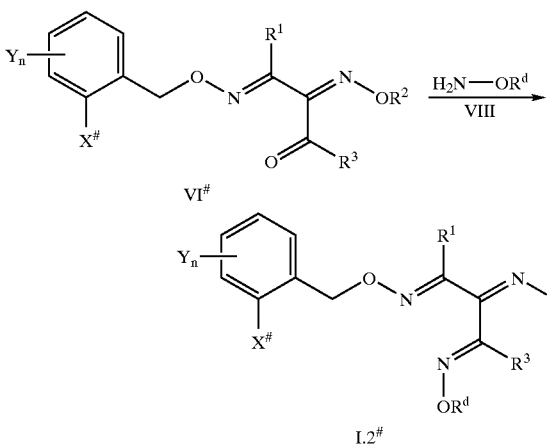

6. The reaction of the carbonyl compound VI# to give the trioxime ether I.2# is normally carried out at from 10° C. to 120° C., preferably 20° C. to 85° C., in an inert organic solvent in the presence or absence of a base [cf. EP-A 386 561].

Suitable solvents are ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, and also dimethylsulfoxide, dimethylformamide and dimethylacetamide, especially preferably methanol and ethanol. Mixtures of these may also be used.

Bases which are suitable are, generally, inorganic compounds such as alkali metal carbonates and alkaline earth metal carbonates such as lithium carbonate, potassium carbonate and calcium carbonate, and also alkali metal hydrogen carbonates such as sodium hydrogen carbonate, alkali metal alkoxides and alkaline earth metal alkoxides such as sodium methoxide, sodium ethoxide, potassium ethoxide, potassium tert-butoxide and dimethoxymagnesium, moreover organic bases, eg. tertiary amines such as trimethylamine, triethylamine, triisopropyl-ethylamine and N-methylpiperidine, pyridine, substituted pyridines such as collidine, lutidine and 4-dimethylamino-pyridine and bicyclic amines. Especially preferred are sodium hydrogen carbonate, pyridine and triethylamine.

The bases are generally employed in catalytic amounts, but they can also be used in equimolar amounts, in an excess or, if appropriate, as the solvent.

The starting materials are generally reacted with each other in equimolar amounts. It may be advantageous for the yield to employ VIII in an excess based on VI#.

The reaction mixtures are worked up in the customary manner, eg. by mixing with water, separating the phases and, if appropriate, purifying the crude products by chromatography. Some of the intermediates and end products are obtained in the form of colorless or pale brown viscous oils which are purified or freed from volatile components under reduced pressure and at a moderately elevated temperature. If the intermediates and end products are obtained as solids, they may also be purified by recrystallization or digestion.

Due to the C═C and C═N double bonds of the compounds I, their preparation may yield E/Z isomer mixtures which may be separated into the individual compounds in the customary manner, for example by crystallization or chromatography.

If the synthesis yields isomer mixtures, however, separation is generally not absolutely necessary since in some cases the individual isomers can be converted into each other during processing for use or upon use (eg. when exposed to light, acids or bases). Such conversions may also take place after use, for example when plants are treated in the treated plant or in the harmful fungus or animal pest to be controlled.

As regards the —N═CR$^1$—C(CR$^3$R$^4$)═NOR$^2$ double bonds, the E,E-isomers of the compounds I are generally preferred with a view to their activity (configuration based on the radical —CH$_2$O— relative to the —C(CR$^3$R$^4$)═NOR$^2$ group, or based on the radical —OR$^2$ relative to the —C(R$^1$)—N═OCH$_2$ group).

In the definitions of the symbols given for the above formulae, collective terms were used which generally represent the following substituents:

halogen: fluorine, chlorine, bromine and iodine;

alkyl: saturated straight-chain or branched hydrocarbon radicals having 1 to 4 or 6 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 4 carbon atoms (as mentioned above), it being possible for some or all of the hydrogen atoms in these groups to be replaced by halogen atoms as mentioned above, eg. $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4 carbon atoms (as mentioned above) which are bonded to the skeleton via an oxygen atom (—O—);

alkenyl: unsaturated straight-chain or branched hydrocarbon radicals having 3 to 4 carbon atoms and a double bond in any position, eg. $C_3$–$C_4$-alkenyl such as 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

haloalkenyl: unsaturated straight-chain or branched hydrocarbon radicals having 3 to 4 carbon atoms and a double bond in any position (as mentioned above), it being possible for some or all of the hydrogen atoms in these groups to be replaced by halogen atoms as mentioned above, in particular fluorine, chlorine and bromine;

alkynyl: straight-chain or branched hydrocarbon groups having 3 to 4 carbon atoms and a triple bond in any position, eg. $C_3$–$C_4$-alkynyl such as ethynyl, 1-propynyl, 2-propynyl, 1-butynyl, 2-butynyl, 3-butynyl and 1-methyl-2-propynyl;

haloalkynyl: unsaturated straight-chain or branched hydrocarbon radicals having 3 to 4 carbon atoms and a triple bond in any position (as mentioned above), it being possible for some or all of the hydrogen atoms in these groups to be replaced by halogen atoms as mentioned above, in particular fluorine, chlorine and bromine;

The addition "substituted or unsubstituted", when referring to the phenyl radical, is intended to express that this radical can be partially or fully halogenated [ie. some or all of the hydrogen atoms of this radical can be replaced by identical or different halogen atoms as mentioned above (preferably fluorine, chlorine or bromine, in particular fluorine or chlorine)] and/or can have attached to them one to four (in particular one to three) of the following radicals:

halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

Especially preferred with a view to their intended use are those compounds of the formula I where $R^a$ is $C_1$–$C_2$-alkyl or $C_1$–$C_2$-alkoxy.

Especially preferred are compounds of the formula IB.

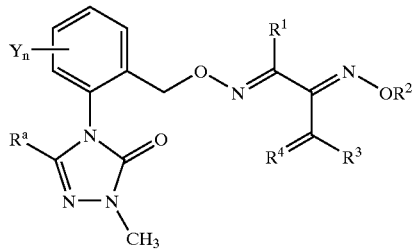

Equally preferred are compounds of the formula I where n=zero (0).

Particularly preferred compounds of the formula I are those where $R^a$ is methyl or methoxy.

Besides these, preferred compounds are those of the formula I.1.

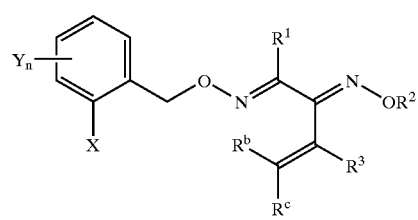

Equally preferred are compounds I.1 where $R^b$ is hydrogen.

Furthermore preferred are compounds of the formula I.2.

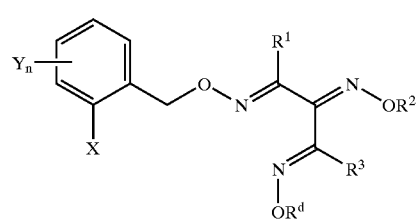

Particularly preferred compounds I.1 are those where $R^3$ and $Y_n$ are hydrogen and $R^2$ is methyl or ethyl.

In addition, especially preferred compounds I.1 are those where $R^3$ is hydrogen, $R^2$ is methyl or ethyl and $Y_n$ is 6-methyl.

Equally, especially preferred compounds I.2 are those where $R^1$ and $R^3$ are methyl, $Y_n$ is hydrogen and $R^2$ is methyl or ethyl.

Besides these, especially preferred compounds I.2 are those where $Y_n$ is 6-methyl.

Particularly preferred with a view to their use are the compounds I which are compiled in the tables which follow. In addition, the groups mentioned in the tables for a substituent are an especially preferred embodiment of the substituent in question, independently of the combination in which they are mentioned.

Table 1

Compounds of the formula I.1A where $R^a$, $R^1$ and $R^2$ are methyl and the combination of the radicals $R^3$, $R^b$ and $R^c$ for a given compound in each case corresponds to one line of Table A

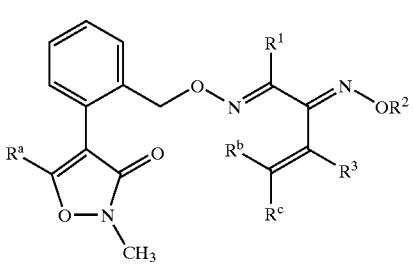

Table 2

Compounds of the formula I.1A where $R^a$ is methoxy, $R^1$ and $R^2$ are methyl and the combination of the radicals $R^3$, $R^b$ and $R^c$ for a given compound in each case corresponds to one line of Table A Table 3

Compounds of the formula I.2A where $R^a$ and $R^1$ are methyl and the combination of the radicals $R^2$, $R^3$ and $R^d$ for

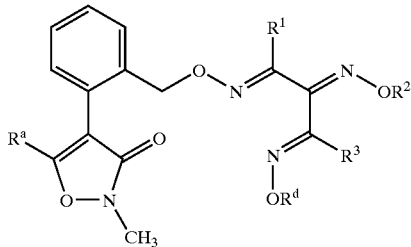

Table 4

Compounds of the formula I.2A where $R^a$ is methoxy, $R^1$ is methyl and the combination of the radicals $R^2$, $R^3$ and $R^d$ for a given compound in each case corresponds to one line of Table B Table 5

Compounds of the formula I.1B where $R^a$, $R^1$ and $R^2$ are methyl and the combination of the radicals $R^3$, $R^b$ and $R^c$ for a given compound in each case corresponds to one line of Table A

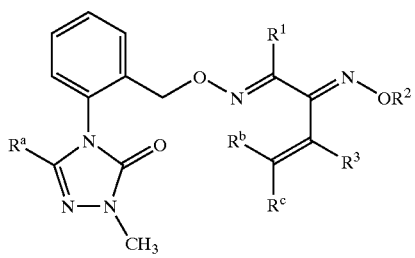

Table 6

Compounds of the formula I.1B where $R^a$ is methoxy, $R^1$ and $R^2$ are methyl and the combination of the radicals $R^3$, $R^b$ and $R^c$ for a given compound in each case corresponds to one line of Table A Table 7

Compounds of the formula I.2B where $R^a$ and $R^1$ are methyl and the combination of the radicals $R^2$, $R^3$ and $R^d$ for a given compound in each case corresponds to one line of Table B

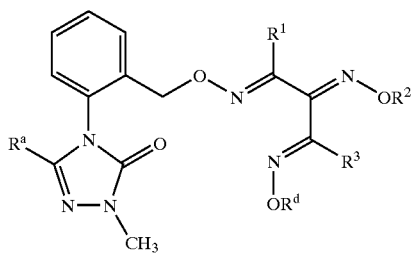

Table 8

Compounds of the formula I.2B where $R^a$ is methoxy, $R^1$ is methyl and the combination of the radicals $R^2$, $R^3$ and $R^d$ for a given compound in each case corresponds to one line of Table B Table 9

Compounds of the formula I.1A where $R^a$ and $R^2$ are methyl, $R^1$ is ethyl and the combination of the radicals $R^3$, $R^b$ and $R^c$ for a given compound in each case corresponds to one line of Table A Table 10

Compounds of the formula I.1A where $R^a$ is methoxy, $R^1$ is ethyl and $R^2$ is methyl and the combination of the radicals $R^3$, $R^b$ and $R^c$ for a given compound in each case corresponds to one line of Table A Table 11

Compounds of the formula I.2A where $R^a$ and $R^1$ are ethyl and the combination of the radicals $R^2$, $R^3$ and $R^d$ for a given compound in each case corresponds to one line of Table B Table 12

Compounds of the formula I.2A where $R^a$ is methoxy and $R^1$ is ethyl and the combination of the radicals $R^2$, $R^3$ and $R^d$ for a given compound in each case corresponds to one line of Table B Table 13

Compounds of the formula I.1B where $R^a$ and $R^2$ are methyl, $R^1$ is ethyl and the combination of the radicals $R^3$, $R^b$ and $R^c$ for a given compound in each case corresponds to one line of Table A Table 14

Compounds of the formula I.1B where $R^a$ is methoxy, $R^1$ is ethyl and $R^2$ is methyl and the combination of the radicals $R^3$, $R^b$ and $R^c$ for a given compound in each case corresponds to one line of Table A Table 15

Compounds of the formula I.2B where $R^a$ and $R^1$ are ethyl and the combination of the radicals $R^2$, $R^3$ and $R^d$ for a given compound in each case corresponds to one line of Table B Table 16

Compounds of the formula I.2B where $R^a$ is methoxy and $R^1$ is ethyl and the combination of the radicals $R^2$, $R^3$ and $R^d$ for a given compound in each case corresponds to one line of Table B Table 17

Compounds of the formula I.1Ba where $R^a$ is methoxy, $R^1$ and $R^2$ are methyl and the combination of the radicals $R^3$, $R^b$ and $R^c$ for a given compound in each case corresponds to one line of Table A

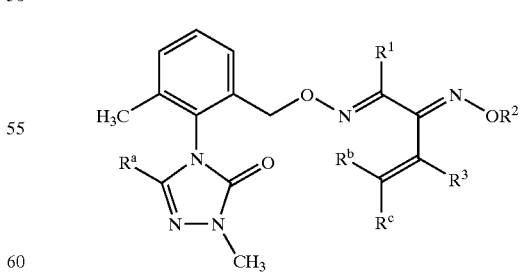

Table 18

Compounds of the formula I.2Ba where $R^a$ is methoxy and $R^1$ is methyl and the combination of the radicals $R^2$, $R^3$ and $R^d$ for a given compound in each case corresponds to one line of Table A

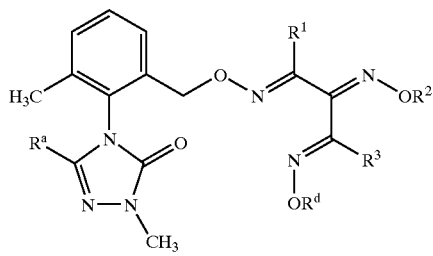

I.2Ba

TABLE A

| No. | $R^a$ | $R^b$ | $R^c$ |
|---|---|---|---|
| A-1 | H | H | H |
| A-2 | H | H | $CH_3$ |
| A-3 | H | H | $CH_2CH_3$ |
| A-4 | H | H | $CH_2CH_2CH_3$ |
| A-5 | H | H | $CH(CH_3)_2$ |
| A-6 | H | H | $C(CH_3)_3$ |
| A-7 | H | H | $CH_2C_6H_5$ |
| A-8 | H | H | $CH=CH—CH_3$ |
| A-9 | H | H | $C_6H_5$ |
| A-10 | H | H | $4$-$Cl$-$C_6H_4$ |
| A-11 | H | H | $4$-$F$-$C_6H_4$ |
| A-12 | H | $CH_3$ | $CH_3$ |
| A-13 | H | $CH_3$ | $CH_2CH_3$ |
| A-14 | H | $CH_3$ | $CH_2CH_2CH_3$ |
| A-15 | H | $CH_3$ | $CH(CH_3)_2$ |
| A-16 | H | $CH_3$ | $C(CH_3)_3$ |
| A-17 | H | $CH_3$ | $CH_2C_6H_5$ |
| A-18 | H | $CH_3$ | $C_6H_5$ |
| A-19 | H | $CH_3$ | $4$-$Cl$-$C_6H_4$ |
| A-20 | H | $CH_3$ | $4$-$F$-$C_6H_4$ |
| A-21 | $CH_3$ | H | H |
| A-22 | $CH_3$ | H | $CH_3$ |
| A-23 | $CH_3$ | H | $CH_2CH_3$ |
| A-24 | $CH_3$ | H | $CH_2CH_2CH_3$ |
| A-25 | $CH_3$ | H | $CH(CH_3)_2$ |
| A-26 | $CH_3$ | H | $C(CH_3)_3$ |
| A-27 | $CH_3$ | H | $CH_2C_6C_5$ |
| A-28 | $CH_3$ | H | $CH=CH—CH_3$ |
| A-29 | $CH_3$ | H | $C_6H_5$ |
| A-30 | $CH_3$ | H | $4$-$Cl$-$C_6H_4$ |
| A-31 | $CH_3$ | H | $4$-$F$-$C_6H_4$ |
| A-32 | $CH_3$ | $CH_3$ | H |
| A-33 | $CH_3$ | $CH_3$ | $CH_3$ |
| A-34 | $CH_3$ | $CH_3$ | $CH_2CH_3$ |
| A-35 | H | $CH_3$ | H |
| A-36 | H | $CH_2CH_3$ | H |
| A-37 | H | $CH_2CH_2CH_3$ | H |
| A-38 | H | $CH(CH_3)_2$ | H |
| A-39 | H | $C(CH_3)_3$ | H |
| A-40 | H | $CH_2C_6C_5$ | H |
| A-41 | H | $CH=CH—CH_3$ | H |
| A-42 | H | $C_6H_5$ | H |
| A-43 | H | $4$-$Cl$-$C_6H_4$ | H |
| A-44 | H | $4$-$F$-$C_6H_4$ | H |
| A-45 | H | $CH_2CH_3$ | $CH_3$ |
| A-46 | H | $CH_2CH_2CH_3$ | $CH_3$ |
| A-47 | H | $CH(CH_3)_2$ | $CH_3$ |
| A-48 | H | $C(CH_3)_3$ | $CH_3$ |
| A-49 | H | $CH_2C_6C_5$ | $CH_3$ |
| A-50 | H | $C_6H_5$ | $CH_3$ |
| A-51 | H | $4$-$Cl$-$C_6H_4$ | $CH_3$ |
| A-52 | H | $4$-$F$-$C_6H_4$ | $CH_3$ |
| A-53 | $CH_3$ | $CH_2CH_3$ | H |
| A-54 | $CH_3$ | $CH_2CH_2CH_3$ | H |
| A-55 | $CH_3$ | $CH(CH_3)_2$ | H |
| A-56 | $CH_3$ | $C(CH_3)_3$ | H |
| A-57 | $CH_3$ | $CH_2C_6C_5$ | H |
| A-58 | $CH_3$ | $CH=CH—CH_3$ | H |
| A-59 | $CH_3$ | $C_6H_5$ | H |
| A-60 | $CH_3$ | $4$-$CL$-$C_6H_4$ | H |
| A-61 | $CH_3$ | $4$-$F$-$C_6H_4$ | H |
| A-62 | $CH_3$ | $CH_2CH_3$ | $CH_3$ |

TABLE B

| No. | $R^2$ | $R^3$ | $R^d$ |
|---|---|---|---|
| B-1 | $CH_3$ | H | $CH_3$ |
| B-2 | $CH_3$ | H | $CH_2CH_3$ |
| B-3 | $CH_3$ | H | $CH_2CH_2CH_3$ |
| B-4 | $CH_3$ | H | $CH(CH_3)_2$ |
| B-5 | $CH_3$ | H | $C(CH_3)_3$ |
| B-6 | $CH_3$ | H | $CH_2CH=CH_2$ |
| B-7 | $CH_3$ | H | $CH_2C\equiv CH$ |
| B-8 | $CH_3$ | H | $CH_2CH_2CH_2CH_3$ |
| B-9 | $CH_3$ | $CH_3$ | $CH_3$ |
| B-10 | $CH_3$ | $CH_3$ | $CH_2CH_3$ |
| B-11 | $CH_3$ | $CH_3$ | $CH_2CH_2CH_3$ |
| B-12 | $CH_3$ | $CH_3$ | $CH(CH_3)_2$ |
| B-13 | $CH_3$ | $CH_3$ | $C(CH_3)_3$ |
| B-14 | $CH_3$ | $CH_3$ | $CH_2CH=CH_2$ |
| B-15 | $CH_3$ | $CH_3$ | $CH_2C\equiv CH$ |
| B-16 | $CH_3$ | $CH_3$ | $CH_2CH_2CH_2CH_3$ |
| B-17 | $CH_3$ | $CH_2CH_3$ | $CH_3$ |
| B-18 | $CH_3$ | $CH_2CH_3$ | $CH_2CH_3$ |
| B-19 | $CH_3$ | $CH_2CH_3$ | $CH_2CH_2CH_3$ |
| B-20 | $CH_3$ | $CH_2CH_3$ | $CH(CH_3)_2$ |
| B-21 | $CH_3$ | $CH_2CH_3$ | $C(CH_3)_3$ |
| B-22 | $CH_3$ | $CH_2CH_3$ | $CH_2CH=CH_2$ |
| B-23 | $CH_3$ | $CH_2CH_3$ | $CH_2C\equiv CH$ |
| B-24 | $CH_3$ | $CH_2CH_3$ | $CH_2CH_2CH_2CH_3$ |
| B-25 | $CH_2CH_3$ | H | $CH_3$ |
| B-26 | $CH_2CH_3$ | H | $CH_2CH_3$ |
| B-27 | $CH_2CH_3$ | H | $CH_2CH_2CH_3$ |
| B-28 | $CH_2CH_3$ | H | $CH(CH_3)_2$ |
| B-29 | $CH_2CH_3$ | H | $C(CH_3)_3$ |
| B-30 | $CH_2CH_3$ | H | $CH_2CH=CH_2$ |
| B-31 | $CH_2CH_3$ | H | $CH_2C\equiv CH$ |
| B-32 | $CH_2CH_3$ | H | $CH_2CH_2CH_2CH_3$ |
| B-33 | $CH_2CH_3$ | $CH_3$ | $CH_3$ |
| B-34 | $CH_2CH_3$ | $CH_3$ | $CH_2CH_3$ |
| B-35 | $CH_2CH_3$ | $CH_3$ | $CH_2CH_2CH_3$ |
| B-36 | $CH_2CH_3$ | $CH_3$ | $CH(CH_3)_2$ |
| B-37 | $CH_2CH_3$ | $CH_3$ | $C(CH_3)_3$ |
| B-38 | $CH_2CH_3$ | $CH_3$ | $CH_2CH=CH_2$ |
| B-39 | $CH_2CH_3$ | $CH_3$ | $CH_2C\equiv CH$ |
| B-40 | $CH_2CH_3$ | $CH_3$ | $CH_2CH_2CH_2CH_3$ |
| B-41 | $CH_2CH_3$ | $CH_2CH_3$ | $CH_3$ |
| B-42 | $CH_2CH_3$ | $CH_2CH_3$ | $CH_2CH_3$ |
| B-43 | $CH_2CH_3$ | $CH_2CH_3$ | $CH_2CH_2CH_3$ |
| B-44 | $CH_2CH_3$ | $CH_2CH_3$ | $CH(CH_3)_2$ |
| B-45 | $CH_2CH_3$ | $CH_2CH_3$ | $C(CH_3)_3$ |
| B-46 | $CH_2CH_3$ | $CH_2CH_3$ | $CH_2CH=CH_2$ |
| B-47 | $CH_2CH_3$ | $CH_2CH_3$ | $CH_2C\equiv CH$ |
| B-48 | $CH_2CH_3$ | $CH_2CH_3$ | $CH_2CH_2CH_2CH_3$ |

The compounds I are suitable as fungicides. They are distinguished by an outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,

*Botrytis cinerea* (gray mold) on strawberries, vegetables, ornamentals and grapevines,

*Cercospora arachidicola* on peanuts,

*Erysiphe cichoracearum* and *Sphaerotheca fuliginea* on cucurbits,

*Erysiphe graminis* (powdery mildew) on cereals,

Fusarium and Verticillium species on various plants,

Helminthosporium species on cereals,

Mycosphaerella species on bananas,

*Phytophthora infestans* on potatoes and tomatoes,

*Plasmopara viticola* on grapevines,

*Podosphaera leucotricha* on apples,

*Pseudocercosporella herpotrichoides* on wheat and barley,

Pseudocercosporella species on hops and cucumbers,

Puccinia species on cereals,

*Pyricularia oryzae* on rice,

Rhizoctonia species on cotton, rice and lawns,

*Septoria nodorum* on wheat,

*Uncinula necator* on grapevines,

Ustilago species on cereals and sugar cane, and

*Venturia inaequalis* (scab) on apples.

Moreover, the compounds I are suitable for controlling harmful fungi such as *Paecilomyces variotii* in the protection of materials (eg. wood, paper, paint dispersions, fibers and woven tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and of the effect desired. Rates of application conventionally used in the protection of materials are, for example, from 0.001 g to 2 kg, preferably 0.005 g to 1 kg, of active ingredient per cubic meter of material treated.

Moreover, the compounds of the formula I are suitable for efficiently controlling animal pests from the classes of the insects, arachnids and nematodes. They can be employed in crop protection and in the hygiene, stored-product and veterinary sector for controlling animal pests. In particular, they are suitable for controlling the following animal pests:

insects from the order of the lepidopterans (Lepidoptera), eg. *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), eg. *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria,* dipterans (Diptera), eg. *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* thrips (Thysanoptera), eg. *Frankliniella fusca, Frankliniella occidentalis, Frankliniella tritici, Scirtothrips citri, Thrips oryzae, Thrips palmi* and *Thrips tabaci,* hymenopterans (Hymenoptera), eg. *Athalia rosae, Atta cephalotes, Atta sexdens, Atta texana, Hoplocampa minuta, Hoplocampa testudinea, Monomorium pharaonis, Solenopsis geminata* and *Solenopsis invicta,* heteropterans (Heteroptera), eg. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterans (Homoptera), eg. *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* termites (Isoptera), eg. *Calotermes flavicollis, Leucotermes flavipes, Reticulitermes lucifugus* and *Termes natalensis,* orthopterans (Orthoptera), eg. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,*

Arachnoidea, such as arachnids (Acarina), eg. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root knot nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The rate of application of active ingredient for controlling animal pests is from 0.1 to 2.0, preferably 0.2 to 1.0, kg/ha under field conditions.

The compounds I can be converted into the customary formulations, eg. solutions, emulsions, suspensions, dusts, powders, pastes and granules. The use form depends on the particular purpose; in any case, it should guarantee a fine and uniform distribution of the compound according to the invention.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:
 I. 5 parts by weight of a compound according to the invention are mixed intimately with 95 parts by weight of finely divided kaolin. This gives a dust which comprises 5% by weight of the active ingredient.
 II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of active ingredient.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, which concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

In the use form as fungicides, the compositions according to the invention can also be present together with other active ingredients, eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis-(dimethylamino)phosphinyl]-3-phenyl-1,2,4-triazole, 2,3-dicyano-1,4-dithioanthraquinone, 2-thio-1,3-dithiolo [4,5-b] quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1, 2,2-tetrachloroethylthio)tetrahydrophthalimide, N-trichloromethylthio-tetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4- oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichlorethane;

amines such as 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, (8-(1,1-dimethylethyl)-N-ethyl-N-propyl-1,4-dioxaspiro[4.5]decane-2-methanamine;

azoles such as 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, 1-[2-(2,4-dichlorophenyl)pentyl]-1H-1,2,4-triazole, 2,4'-difluoro-α-(1H-1,2,4-triazolyl-1-methyl)benzhydryl alcohol, 1-((bis-(4-fluorophenyl) methylsilyl)methyl)-1H-1,2,4-triazole, 1-[2RS,4RS;2RS,4SR)-4-bromo-2-(2,4-dichlorophenyl) tetrahydrofuryl]-1H-1,2,4-triazole, 2-(4-chlorophenyl)-3-cyclopropyl-1-(1H-1,2,4-triazol-1-yl)butan-2-ol, (+)-4-chloro-4-[4-methyl-2-(1H-1,2,4-triazol-1-yl-methyl)-1,3-dioxolan-2-yl]-phenyl-4-chlorophenyl ether, (E)-(R,S)-1-(2,4-dichlorophenyl)-4,4-dimethyl-2-(1H-1,2,-4-triazol-1-yl)pent-1-en-3-ol, 4-(4-chlorophenyl)-2-phenyl-2-(1H-1,2,4-triazolylmethyl) butyronitrile, 3-(2,4-dichlorophenyl)-6-fluoro-2-(1H-1,2,4-triazol-1-yl)quinazolin-4(3H)-one, (R,S)-2-(2,4-dichlorophenyl)-1H-1,2,4-triazol-1-yl)hexan-2-ol, (1RS,5RS;1RS,5SR)-5-(4-chlorobenzyl)-2,2-dimethyl-1-(1H-1,2,4-triazol-1-ylmethyl) cyclopentanol, (R,S)-1-(4-chlorophenyl)-4,4-dimethyl-3-(1H-1,2,4-triazol-1-ylmethyl)pentan-3-ol, (+)-2-(2,4-dichlorophenyl)-3-(1H-1,2,4-triazolyl)propyl-1,1,2,2-tetrafluoroethyl ether, (E)-1-[1-[4-chloro-2-trifluoromethyl)phenyl]imino)-2-propoxyethyl]-1H-imidazole, 2-(4-chlorophenyl)-2-(1H-1,2,4-triazol-1-ylmethyl)hexanonitrile;

α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins such as methyl E-methoxyimino-[α-(o-tolyloxy)-o-tolyl]acetate, methyl E-2-{2-[6-(2-cyanophenoxy)pyrimidin-4-yloxy]-phenyl}-3-methoxyacrylate, N-methyl-E-methoxyimino-[α-(2-phenoxyphenyl)]-acetamide, methyl E-methoxyimino-[α-(2,5-dimethylphenoxy)-o-tolyl]acetamide, anilinopyrimidines such as N-(4,6-dimethylpyrimidin-2-yl)aniline, N-[4-methyl-6-(1-propynyl)pyrimidin-2-yl] aniline, N-[4-methyl-6-cyclopropylpyrimidin-2-yl] aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acryloylmorpholine, and a variety of fungicides such as dodecylguanidine acetate, 3-[3-(3,5-dimethyl-2-oxycyclohexyl)-2-hydroxyethyl]glutarimide, N-methyl-N-ethyl-(4-trifluoromethyl-2-[3',4'-dimethoxyphenyl]-benzamide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, N-(3-chloro-2,6-dinitro-4-trifluoromethylphenyl)-5-trifluoromethyl-3-chloro-2-aminopyridine.

SYNTHESIS EXAMPLES

With due modification of the starting compounds, the protocols shown in the synthesis examples below were used for obtaining further compounds I. The resulting compounds, together with physical data, are listed in the Tables which follow.

Example 1

Preparation of

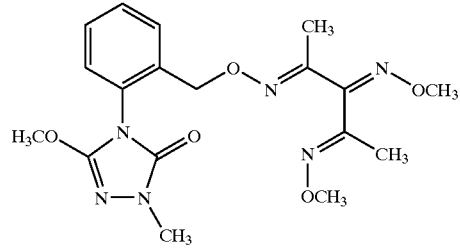

Method A:

A solution of 1.1 g of 4-[(2-bromomethyl)phenyl]-2,4-dihydro-5-methoxy-2-methyl-3H-1,2,4-triazol-3-one [cf. WO-A 97/00,612], 1.35 g of potassium carbonate and 0.68 g of 2,3,4-pentanetrione 2-(E)-3-(Z)-bis(O-methyloxime)-4-(E)-oxime (cf. DE-A 195 39 324] in 35 ml of dimethylformamide (DMF) was stirred at 25–35° C. for 8 h. The reaction mixture was then poured onto ice-water and extracted with methyl tert-butyl ether and the combined organic phases were washed with sat. ammonium chloride solution and dried. The solvent was distilled off and the residue was subjected to silica gel chromatography (cyclohexane/ethyl acetate 80:20), giving 400 mg of product as a clear powder of mp. 142–145° C.

IR (cm−1): 1715, 1611, 1502, 1481, 1415, 1049, 999, 988, 895.

Method B:

1.1 g of 4-[(2-bromomethyl)phenyl]-2,4-dihydro-5-chloro-2-methyl-3H-1,2,4-triazol-3-one [cf. WO-A 97/19935, Table B, p. 23, comp. No. 77], dissolved in 15 ml of DMF, were stirred with 1.35 g of potassium carbonate and 0.68 g of 2,3,4-pentanetrione 2-(E)-3-(Z)-bis(O-methyloxime)-4-(E)-oxime [cf. DE-A 195 39 324] at 22–25° C. for approximately 12 h. The reaction mixture was then poured onto ice-water and extracted with methyl tert-butyl ether and the combined organic phases were washed with sat. ammonium chloride solution and dried. The solvent was distilled off and the residue was subjected to silica gel chromatography (cyclohexane/ethyl acetate 80:20). The crude product (700 mg) was dissolved in 5 ml of dimethoxyethane and 5 ml of methanol and admixed with 0.61 g of a 30% strength methanolic sodium methoxide solution. The reaction mixture was heated under reflux for approximately 20 h, taken up in methylene chloride, washed with water and sat. ammonium chloride solution and then dried. The solvent was distilled off and the residue was subjected to silica gel chromatography (cyclohexane/ethyl acetate 80:20), giving 300 mg of the title compound as a clear powder of mp. 142–145° C.

IR (cm−1): 1715, 1611, 1502, 1481, 1415, 1049, 999, 988, 895.

TABLE I

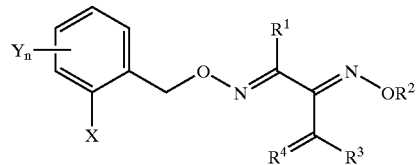

| No. | X | $Y_n$ | $R^1$ | $R^2$ | $R^3$ | $R^4$ | Phys. data (mp. [° C.]) |
|---|---|---|---|---|---|---|---|
| I-1 | B ($R^a$ = $OCH_3$) | H | $CH_3$ | $CH_3$ | H | =C($CH_3$)$_2$ | 92–95 |
| I-2 | B ($R^a$ = $OCH_3$) | H | $CH_3$ | $CH_3$ | $CH_3$ | =NOCH$_3$ | 142–145 |

Examples of the Action Against Harmful Fungi

The fungicidal action of the compounds of the formula I was demonstrated by the following experiments:

The active ingredients were formulated separately or jointly as a 10% emulsion in a mixture of 70% by weight of cyclohexanone, 20% by weight of Nekanil® LN (Lutensol® AP6, wetter with emulsifying and dispersing action based on ethoxylated alkylphenols) and 10% by weight of Wettol® EM (non-ionic emulsifier based on ethoxylated castor oil) and diluted with water to suit the desired concentration.

Use Example 1—Activity Against Powdery Mildew of Wheat

Leaves of potted wheat seedlings c.v. "Frühgold" were sprayed to runoff point with an aqueous preparation of active ingredient made from a stock solution comprising 10% of active ingredient, 63% of cyclohexanone and 27% of emulsifier, and, 24 hours after the spray coating had dried on, dusted with spores of powdery mildew of wheat (*Erysiphe graminis* forma specialis tritici). The test plants were subsequently kept in a greenhouse at from 20 to 24° C. and from 60 to 90% relative atmospheric humidity. After 7 days, the extent of the mildew development was determined visually as % infection of the total leaf area.

Use Example 2—Activity Against *Pyricularia oryzae* (Protective)

Leaves of potted rice seedlings c.v. "Tai-Nong 67" were sprayed to runoff point with an aqueous preparation of active ingredient made from a stock solution comprising 10% of active ingredient, 63% of cyclohexanone and 27% of emulsifier. The following day, the plants were inoculated with an aqueous spore suspension of *Pyricularia oryzae*. The test plants were subsequently kept in climatized chambers at 22–24° C. and 95–99% relative atmospheric humidity for 6 days. The extent of the development of the infection on the leaves was then determined visually.

In these tests, the plants which had been treated with 16 ppm of the compound No. I-1 of Table I showed at most 5% infection, whereas the untreated plants were infected to 80 or 85%.

Examples of the Action Against Animal Pests

The action of the compounds of the formula I against animal pests was demonstrated by the following experiments:

The active ingredients were formulated
a. as a 0.1% strength solution in acetone or
b. as a 10% emulsion in a mixture of 70% by weight of cyclohexanone, 20% by weight of Nekanil® LN (Lutensol® AP6, wetter with emulsifying and dispersing action based on ethoxylated alkylphenols) and 10% by weight of Wettol® EM (non-ionic emulsifier based on ethoxylated castor oil)

and diluted to give the desired concentration, using acetone in the case of a. and water in the case of b.

After the experiments had been concluded, in each case the lowest concentration was determined at which the compounds still caused an 80 to 100% inhibition or mortality in comparison with untreated controls (limit or minimal concentration).

We claim:

1. A bisimino-substituted phenyl compound of formula I

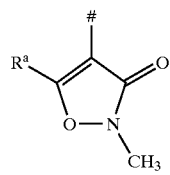

wherein
X is a group A or B

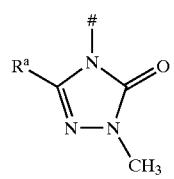

where
# denotes the bond with the phenyl ring and
$R^a$ is halogen, $C_1$–$C_4$-alkyl or $C_1$–$C_4$-alkoxy;
Y is halogen, $C_1$–$C_4$-alkyl, $C_1$–$C_4$-haloalkyl or $C_1$–$C_4$-alkoxy;

n is 0, 1 or 2, wherein the radicals Y are identical or different when n is 2;

$R^1$ is $C_1$–$C_4$-alkyl;

$R^2$ is $C_1$–$C_4$-alkyl, $C_1$–$C_4$-haloalkyl, $C_3$–$C_4$-alkenyl, $C_3$–$C_4$-haloalkenyl, $C_3$–$C_4$-alkynyl or $C_3$–$C_4$-haloalkynyl;

$R^3$ is hydrogen, $C_1$–$C_4$-alkyl, $C_1$–$C_4$-haloalkyl or substituted or unsubstituted phenyl;

$R^4$ is =$CR^bR^c$ or =N—$OR^d$ where $R^b$, $R^c$ independently of one another are hydrogen, $C_1$–$C_6$-alkyl or substituted or unsubstituted phenyl;

$R^d$ is $C_1$–$C_4$-alkyl, $C_{1-4}$-haloalkyl, $C_3$–$C_4$-alkenyl, $C_3$–$C_4$-haloalkenyl, $C_3$–$C_4$-alkynyl or $C_3$–$C_4$-haloalkynyl;

and wherein the phenyl radical represented by $R^3$, $R^b$ or $R^c$ is unsubstituted or is partially or fully halogenated, or carries, optionally in addition to the halogen substituents, one to four radicals selected from the group consisting of: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

2. A process for the preparation of the compound of formula I defined in claim 1 wherein $R^4$ denotes the $CR^bR^c$ group, which comprises reacting a benzyl compound of formula II

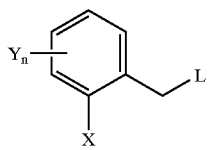

II where L is a nucleophilically exchangeable group with an oxime of formula III

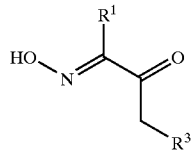

III and converting the resulting oxime ether of formula IV

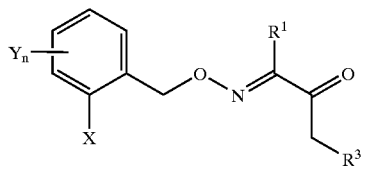

IV into a halogen compound of formula V

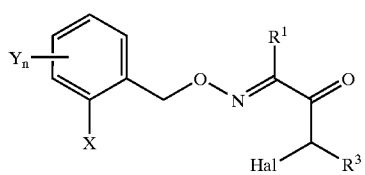

V by means of halogenation, reacting V with a hydroxylamine ether of formula VI'

VI' to give a bisoxime of formula VI,

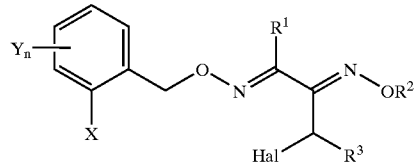

VI oxidizing VI to give a carbonyl compound of formula VII

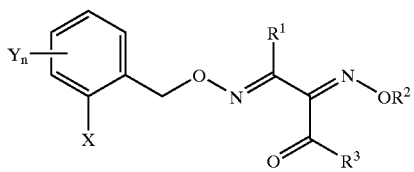

VII and reacting VII with a phosphorus reagent following the principles of a wittig reaction.

3. A process for the preparation of the compound of formula I defined in claim 1 wherein $R^4$ denotes the $NOR^d$ group, which comprises reacting a carbonyl compound of formula VII

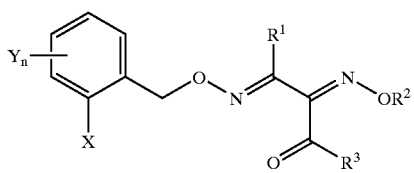

VII with a hydroxylamine ether of formula VIII

VII.

4. A carbonyl compound of formula VII

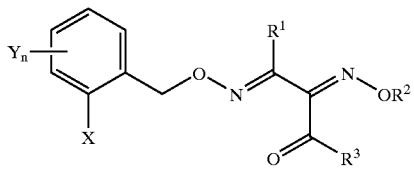

VII wherein

X is a group A or B

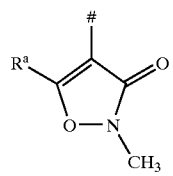

A

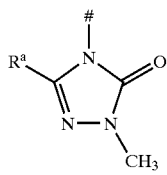

where
# denotes the bond with the phenyl ring and
$R^a$ is halogen, $C_1$–$C_4$-alkyl or $C_1$–$C_4$-alkoxy;

Y is halogen, $C_1$–$C_4$-alkyl, $C_1$–$C_4$-haloalkyl or $C_1$–$C_4$-alkoxy;

n is 0, 1 or 2, wherein the radicals Y are identical or different when n is 2;

$R^1$ is $C_1$–$C_4$-alkyl;

$R^2$ is $C_1$–$C_4$-alkyl, $C_1$–$C_4$-haloalkyl, $C_3$–$C_4$-alkenyl, $C_3$$C_4$-haloalkenyl, $C_3$–$C_4$-alkynyl or $C_3$–$C_4$-haloalkynyl;

$R^3$ is hydrogen, $C_1$–$C_4$-alkyl, $C_1$–$C_4$-haloalkyl or phenyl which is unsubstituted or is partially or fully halogenated, or carries, optionally in addition to the halogen substituents, one to four radicals selected from the group consisting of: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

5. A composition which is suitable for controlling animal pests or harmful fungi, comprising a solid or liquid carrier and the compound of formula I defined in claim 1.

6. A method of controlling harmful fungi, which comprises treating the fungi, or materials, plants, soil or seeds to be protected against fungal infection, with an effective amount of the compound of formula I defined in claim 1.

7. A method of controlling animal pests, which comprises treating the animal pests, or materials, plants, soil or seeds to be protected against said pests, with an effective amount of the compound of formula I defined in claim 1.

8. The compound of formula I defined in claim 1, wherein the phenyl radical represented by $R^3$, $R^b$ or $R^c$ is unsubstituted or is partially or fully halogenated, or carries, optionally in addition to the halogen substituents, one to four radicals selected from the group consisting of: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

9. A compound of formula I defined in claim 1, wherein $R^a$ represents a $C_1$–$C_2$-alkyl or a $C_1$–$C_2$-alkoxy group.

10. The compound of formula I defined in claim 1, wherein $R^a$ represents methyl or methoxy.

11. The compound of formula I defined in claim 1, wherein n is 0.

12. The compound of formula I defined in claim 1, wherein X represents the group B.

13. The compound of formula I defined in claim 1, wherein $R^4$ represents the $CR^bR^c$ group.

14. The compound of formula I defined in claim 13, wherein $R^b$ denotes hydrogen.

15. The compound of formula I defined in claim 13, wherein $R^2$ is methyl or ethyl, and $Y_n$ represents hydrogen or a 6-methyl group.

16. The compound of formula I defined in claim 1, wherein $R^4$ represents the $NOR^d$ group.

17. The compound of formula I defined in claim 16, wherein $R^1$ and $R^3$ are methyl, $Y_n$ represents hydrogen, and $R^2$ is methyl or ethyl.

18. The compound of formula I defined in claim 16, wherein $Y_n$ represents a 6-methyl group.

19. The process of claim 2, wherein the nucleophilically exchangeable group L denotes halogen, or an alkyl or aryl sulfonate.

20. The process of claim 2, wherein the nucleophilically exchangeable group L denotes chlorine, bromine, methylsylate or tosylate.

* * * * *